United States Patent
Kushida

(10) Patent No.: US 11,532,401 B2
(45) Date of Patent: Dec. 20, 2022

(54) RISK EVALUATION SYSTEM AND RISK EVALUATION METHOD

(71) Applicant: Panasonic Intellectual Property Management Co., Ltd., Osaka (JP)

(72) Inventor: Yuki Kushida, Kyoto (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 276 days.

(21) Appl. No.: 16/819,238

(22) Filed: Mar. 16, 2020

(65) Prior Publication Data
US 2020/0219623 A1    Jul. 9, 2020

Related U.S. Application Data

(63) Continuation of application No. PCT/JP2019/001165, filed on Jan. 17, 2019.

(30) Foreign Application Priority Data

Feb. 14, 2018  (JP) .............................. JP2018-023640

(51) Int. Cl.
*G16H 50/30* (2018.01)
*G06T 7/70* (2017.01)
(Continued)

(52) U.S. Cl.
CPC .............. *G16H 50/30* (2018.01); *G01S 17/46* (2013.01); *G06Q 10/06315* (2013.01);
(Continued)

(58) Field of Classification Search
CPC ........ G16H 50/30; G16H 40/20; G16H 50/80; G01S 17/46; G06Q 10/06315; G06T 7/70;
(Continued)

(56) References Cited

U.S. PATENT DOCUMENTS

2010/0164728 A1* 7/2010 Plost .................... G08B 21/245
                                                        340/573.1
2010/0328443 A1* 12/2010 Lynam .................. G06V 20/52
                                                        348/E7.085

(Continued)

FOREIGN PATENT DOCUMENTS

| JP | 2010-230399 | 10/2010 |
| JP | 2013-245090 | 12/2013 |
| JP | 2017-199289 | 11/2017 |

OTHER PUBLICATIONS

Shhedi et al., Traditional & ICT Solution for preventing the Hospital Acquired Infection, 2015, 20th INternational Conference on Control Systems and Science (Year: 2015).*

(Continued)

*Primary Examiner* — Evangeline Barr
*Assistant Examiner* — Karen A Hranek
(74) *Attorney, Agent, or Firm* — Wenderoth, Lind & Ponack, LLP

(57) ABSTRACT

A risk evaluation system is provided with an imager and a controller. The imager takes images at different times of equipment having zones that do not overlap each other, and outputs the images that are taken. The controller detects a contact count of a number of times a living body contacts each of the zones in accordance with the images, decides evaluation information about a contact infection risk in each of the zones in accordance with the contact count, and outputs the evaluation information.

10 Claims, 12 Drawing Sheets

(51) Int. Cl.
*G16H 40/20* (2018.01)
*G01S 17/46* (2006.01)
*G06Q 10/06* (2012.01)
*G06V 40/10* (2022.01)
*G06V 40/20* (2022.01)

(52) U.S. Cl.
CPC .............. *G06T 7/70* (2017.01); *G06V 40/10* (2022.01); *G06V 40/20* (2022.01); *G16H 40/20* (2018.01); *G06T 2207/30196* (2013.01)

(58) Field of Classification Search
CPC . G06T 2207/30196; G06T 2207/10016; G06T 2207/30232; G06V 40/10; G06V 40/20; G06V 20/52; G06V 40/28; G08B 21/245; A61G 12/00; A61B 2090/0803; A61L 2202/24–25
See application file for complete search history.

(56) References Cited

U.S. PATENT DOCUMENTS

| | | | | |
|---|---|---|---|---|
| 2011/0316695 | A1* | 12/2011 | Li | G01S 5/02 340/539.13 |
| 2012/0268277 | A1* | 10/2012 | Best | G08B 21/245 340/573.1 |
| 2013/0187775 | A1* | 7/2013 | Marsden | G16Z 99/00 340/540 |
| 2014/0186221 | A1* | 7/2014 | Yukimoto | A61L 2/18 422/111 |
| 2014/0241571 | A1* | 8/2014 | Bilet | G06T 7/0004 382/103 |
| 2015/0287182 | A1* | 10/2015 | Herger | G16H 30/20 382/128 |
| 2016/0171179 | A1* | 6/2016 | Donofrio | G16H 15/00 705/2 |
| 2016/0306934 | A1* | 10/2016 | Sperry | C12Q 1/04 |
| 2017/0315674 | A1 | 11/2017 | Kamamor | |
| 2017/0336891 | A1* | 11/2017 | Rosenberg | G01S 17/08 |

OTHER PUBLICATIONS

Takahashi et al., Handrail IoT Sensor for Precision Healthcare of Elderly People in Smart Homes, Oct. 2017, IEEE INternational Symposium on Robotics and Intelligent Sensors (Year: 2017).*
International Search Report of PCT application No. PCT/JP2019/001165 dated Mar. 26, 2019.

* cited by examiner

FIG. 4A

| EQUIPMENT | ZONE | START POINT (m) | END POINT (m) |
|---|---|---|---|
| HANDRAIL | 1ST ZONE | 0 | 1 |
| | 2ND ZONE | 1 | 2 |
| | 3RD ZONE | 2 | 3 |
| | ... | ... | ... |
| ... | ... | ... | ... |

FIG. 4B

| EQUIPMENT | ZONE | CONTACT COUNT | BREAKDOWN |
|---|---|---|---|
| HANDRAIL | 1ST ZONE | 4 | 2017/12/2 11:35, 2017/12/2 16:22, 2017/12/3 10:35, 2017/12/3 12:22 |
| | 2ND ZONE | 2 | 2017/12/2 8:35, 2017/12/2 14:10 |
| | 3RD ZONE | 0 | |
| | ... | ... | ... |
| ... | ... | ... | ... |

RISK EVALUATION SYSTEM AND RISK EVALUATION METHOD

BACKGROUND

1. Technical Field

The present disclosure relates to lowering the risk of infection by contact with a contaminated spot in a communal living environment such as a nursing home.

2. Description of the Related Art

In recent years, an increasingly aging population has led to increased demand for nursing homes. In a nursing home where the elderly are gathered, infection in particular can easily become a problem. Major routes of transmission for a pathogen (such as bacteria or a virus, for example) include aerial infection, droplet infection, and contact infection. With aerial or droplet infection, infection is established by the inhalation or ingestion of the pathogen suspended in the air. With contact infection, infection is established due to a person using his or her hand to touch a piece of furniture or the like that is contaminated with the pathogen, and then using the hand to touch his or her mouth, nose, or food.

A major countermeasure for protecting against contact infection is cleaning work by a janitor, but Japanese Unexamined Patent Application Publication No. 2013-245090 for example discloses a touch panel that performs a disinfection operation automatically according to the number of times the touch panel has been touched.

SUMMARY

However, with the above technique of the related art, disinfection is limited to a specific piece of equipment (such as the operation panel of a touch panel elevator, for example), and the various pieces of equipment inside a facility cannot be disinfected. Consequently, cleaning work by a janitor is still necessary for other equipment.

Nursing homes in particular have many pieces of equipment that are frequently touched by human hands, such as handrails along hallways and stairs.

For this reason, the amount and duration of the cleaning work by the janitor increases. Furthermore, there is a possibility that the janitor may forget to clean equipment that needs to be cleaned. On the other hand, there is also a possibility that the janitor may clean equipment that does not need to be cleaned.

One non-limiting and exemplary embodiment provides a technique capable of contributing to more efficient cleaning work for reducing contact infection.

In one general aspect, the techniques disclosed here feature a risk evaluation system provided with an imager and a controller. The imager takes images at different times of equipment having zones that do not overlap each other, and outputs the images that are taken. The controller detects a contact count of a number of times a living body contacts each of the zones in accordance with the images, decides evaluation information about a contact infection risk in each of the zones in accordance with the contact count, and outputs the evaluation information.

It should be noted that this general or specific aspect may be realized by an apparatus, a method, an integrated circuit, a computer program, or a computer-readable recording medium, or any selective combination of an apparatus, a system, a method, an integrated circuit, a computer program, and a recording medium. Computer-readable recording media include non-volatile recording media such as compact disc read-only memory (CD-ROM), for example.

According to the present disclosure, more efficient cleaning work for reducing contact infection is possible. Additional benefits and advantages of the disclosed embodiments will become apparent from the specification and drawings.

The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4A is a table illustrating an example of zone information in Embodiment 1;

FIG. 4B is a table illustrating an example of contact information in Embodiment 1;

DETAILED DESCRIPTION

Overview of Present Disclosure

Figure 1:
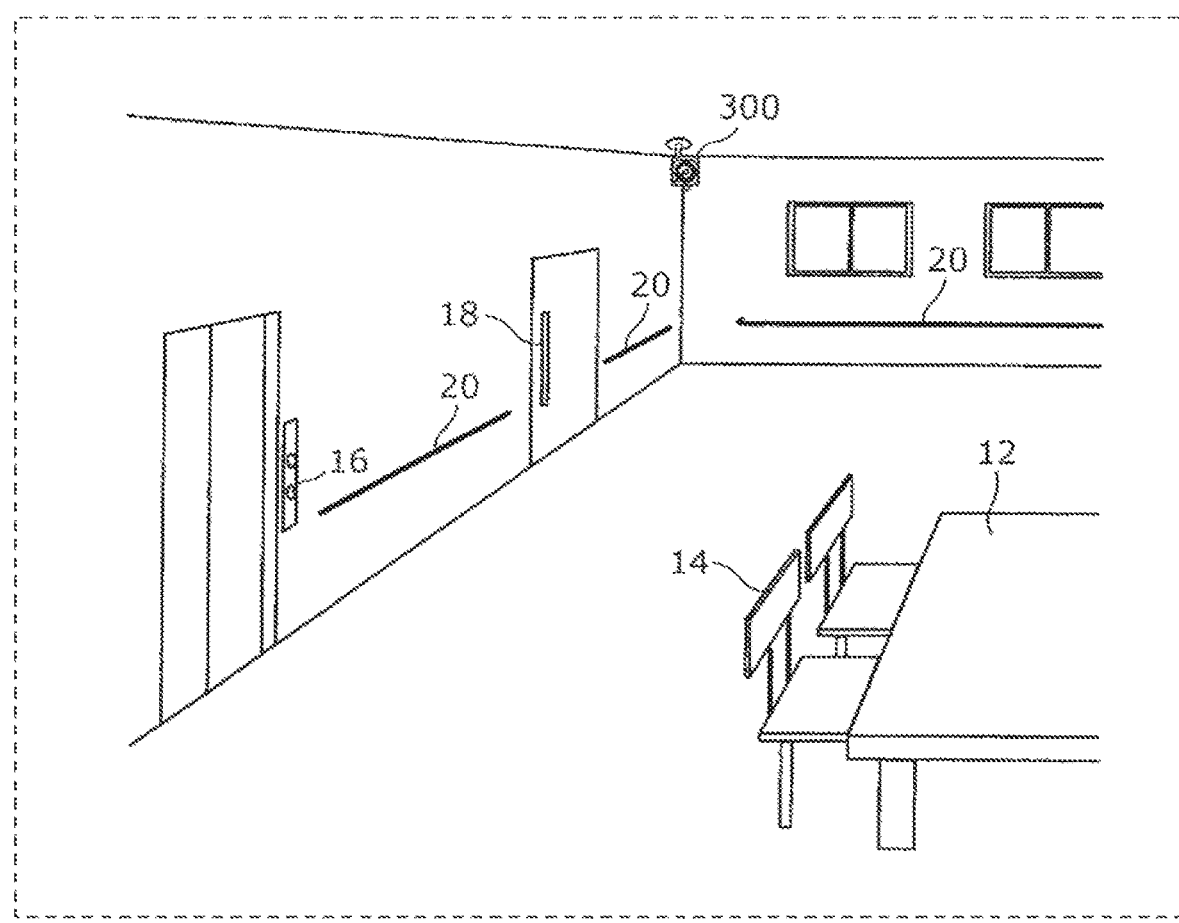
FIG. 1 is a view illustrating an example of equipment inside a building applying a risk evaluation system according to Embodiment 1.

A risk evaluation system according to one aspect of the present disclosure is provided with an imager and a controller. The imager takes images at different times of equipment having zones that do not overlap each other, and outputs the images that are taken. The controller detects a contact count of a number of times a living body contacts each of the zones in accordance with the images, decides evaluation information about a contact infection risk in each of the zones in accordance with the contact count, and outputs the evaluation information.

According to this configuration, it is possible to detect contact with each zone by a living body from images, and output evaluation information about the contact infection risk in each zone in accordance with the detected contact count. Consequently, it is possible to perform cleaning work in each zone according to the evaluation information about the contact infection risk, and contribute to more efficient cleaning work for reducing contact infection.

Also, in the risk evaluation system according to one aspect of the present disclosure, the controller may additionally compute, for each zone, a risk value indicating how high the contact infection risk is in accordance with a number of times contact occurs, and the evaluation information may include the risk value that is computed.

According to this configuration, the risk value computed in accordance with the contact count can be included in the evaluation information.

Consequently, it is possible to perform cleaning work in each zone according to the magnitude of the risk value, and contribute to more efficient cleaning work for reducing contact infection.

Also, in the risk evaluation system according to one aspect of the present disclosure, for each zone, the controller may additionally (i) determine whether or not the risk value that is computed is greater than a predetermined threshold value, and (ii) in a case where the risk value that is computed is greater than the predetermined threshold value, the controller may issue a cleaning instruction to clean the zone.

According to this configuration, it is possible to issue a cleaning instruction in the case where the risk value is greater than a threshold value.

Consequently, an instruction to perform cleaning work in a zone with a high contact infection risk can be issued, and more efficient cleaning work for reducing contact infection can be achieved.

Also, in the risk evaluation system according to one aspect of the present disclosure, the controller may acquire position information about terminal devices, select at least one terminal device among the terminal devices in accordance with the position information about the terminal devices that is acquired, and issue the cleaning instruction to the at least one terminal device that is selected.

According to this configuration, it is possible to issue a cleaning instruction to one or more terminal devices selected from among terminal devices in accordance with position information about the terminal devices. Consequently, the cleaning instruction can be issued to the terminal device of a user capable of performing the cleaning work efficiently according to the positional relationship with the zone, and more efficient cleaning work can be achieved.

Also, in the risk evaluation system according to one aspect of the present disclosure, the controller may additionally (i) determine whether or not detected contact with one of the zones by the living body is contact associated with cleaning work, and (ii) in a case of determining that the detected contact with one of the zones by the living body is the contact associated with the cleaning work, the controller may reset the contact count of the zone to 0.

According to this configuration, in the case of determining that the contact with a zone by a living body is contact associated with cleaning work, the contact count of the zone can be reset to 0. Consequently, the reduction in the contact infection risk achieved by the cleaning work can be reflected in the evaluation information, making it possible to output more accurate evaluation information.

Also, in the risk evaluation system according to one aspect of the present disclosure, in a case of determining that the detected contact with one of the zones by the living body is the contact associated with the cleaning work, the controller may additionally (i) derive a repeat count of motions associated with the cleaning work, and (ii) reset the contact count of the one of the zones to 0 in a case where the repeat count that is derived is greater than a threshold count.

According to this configuration, in the case where a repeat count of motions associated with the cleaning work exceeds a threshold count, the contact count of the zone can be reset to 0. Consequently, in the case where the motion is repeated enough to sufficiently reduce the contact infection risk, the contact count can be reset, and the contact infection risk can be reflected in the evaluation information more accurately.

Also, the risk evaluation system according to one aspect of the present disclosure may be further provided with a terminal device, and the controller may output the evaluation information to the terminal device.

According to this configuration, the risk evaluation system can be provided with a terminal device.

Also, in the risk evaluation system according to one aspect of the present disclosure, the terminal device may display the evaluation information overlaid onto an image of the equipment.

According to this configuration, the evaluation information can be displayed overlaid onto an image of the equipment. Consequently, the janitor can intuitively grasp locations that need to be cleaned, and even more efficient cleaning work can be achieved.

Also, the risk evaluation system according to one aspect of the present disclosure may be further provided with a detector that detects contact by the living body with each of the zones in the equipment having the zones that do not overlap each other. The controller may decide evaluation information about the contact infection risk in each of the zones in accordance with a number of times the contact by the living body is detected by the detector.

According to this configuration, evaluation information about the contact infection risk can be output for each zone in accordance with the contact count detected by the detector. Consequently, it is possible to output more accurate evaluation information.

Also, in the risk evaluation system according to one aspect of the present disclosure, the detector may include a distance sensor that detects a distance to the living body contacting a surface of the equipment, and the controller may specify the contact by the living body and one of the zones that the living body is contacting in accordance with the distance that is detected.

According to this configuration, in accordance with the detected distance, contact by a living body can be detected and the zone that the living body is contacting can be specified. Consequently, the two functions of contact detection and zone specification can be achieved with the distance sensor, and the system configuration can be simplified.

Also, in the risk evaluation system according to one aspect of the present disclosure, the distance sensor may be an optical distance sensor that emits a light beam along the surface of the equipment, and detects the distance to the living body contacting the surface according to the light beam.

Also, in the risk evaluation system according to one aspect of the present disclosure, the equipment may be elongated equipment, and the optical distance sensor may include two optical distance sensors, installed on each end in a longitudinal direction of the equipment, that emit light beams in opposite directions in the longitudinal direction.

According to this configuration, the optical distance sensor can be provided on each end of elongated equipment, and in the case where two living bodies contact the surface of the equipment at the same time, two times of contact can be detected.

It should be noted that these general or specific aspects may be implemented as an apparatus, a method, an integrated circuit, a computer program, a computer-readable recording medium such as a CD-ROM disc, or any selective combination thereof.

Hereinafter, embodiments will be described specifically with reference to the drawings.

Note that the embodiments described hereinafter all illustrate general or specific examples. Features such as numerical values, shapes, materials, structural elements, layout positions and connection states of structural elements, steps, and the ordering of steps indicated in the following embodiments are merely examples, and are not intended to limit the scope of the claims. In addition, among the structural elements in the following embodiments, structural elements that are not described in the independent claim indicating the broadest concept are described as arbitrary or optional structural elements. Also, the diagrams are not necessarily exact illustrations. In the drawings, structural elements that are substantially the same are denoted with the same signs, and duplicate description of such structural elements will be reduced or omitted.

Also, the following embodiments describe a case in which the risk evaluation system is used with equipment inside a nursing home as an example, but the equipment that is usable with the risk evaluation system is not limited to equipment inside a nursing home. For example, the risk evaluation system is also usable with equipment inside a building such as a hospital or an airport, and is furthermore usable with equipment outdoors.

Embodiment 1

[Equipment Inside Nursing Home]

First, the equipment inside a nursing home that is used with a risk evaluation system will be described. FIG. 1 illustrates an example of equipment inside a nursing home used with a risk evaluation system according to Embodiment 1.

In the nursing home of FIG. 1, pieces of equipment including a table 12, chairs 14, a touch panel 16, a door 18, and handrails 20 are installed. The risk evaluation system according to the present embodiment contributes to a reduction in contact infection from person to person via the surfaces of these pieces of equipment and also to more efficient cleaning work of the equipment.

Contact with the surfaces of the equipment by the body (for example, a hand) of a person is detected from an image taken by an imaging unit 300 over time.

[Image Examples]

Figure 2A:
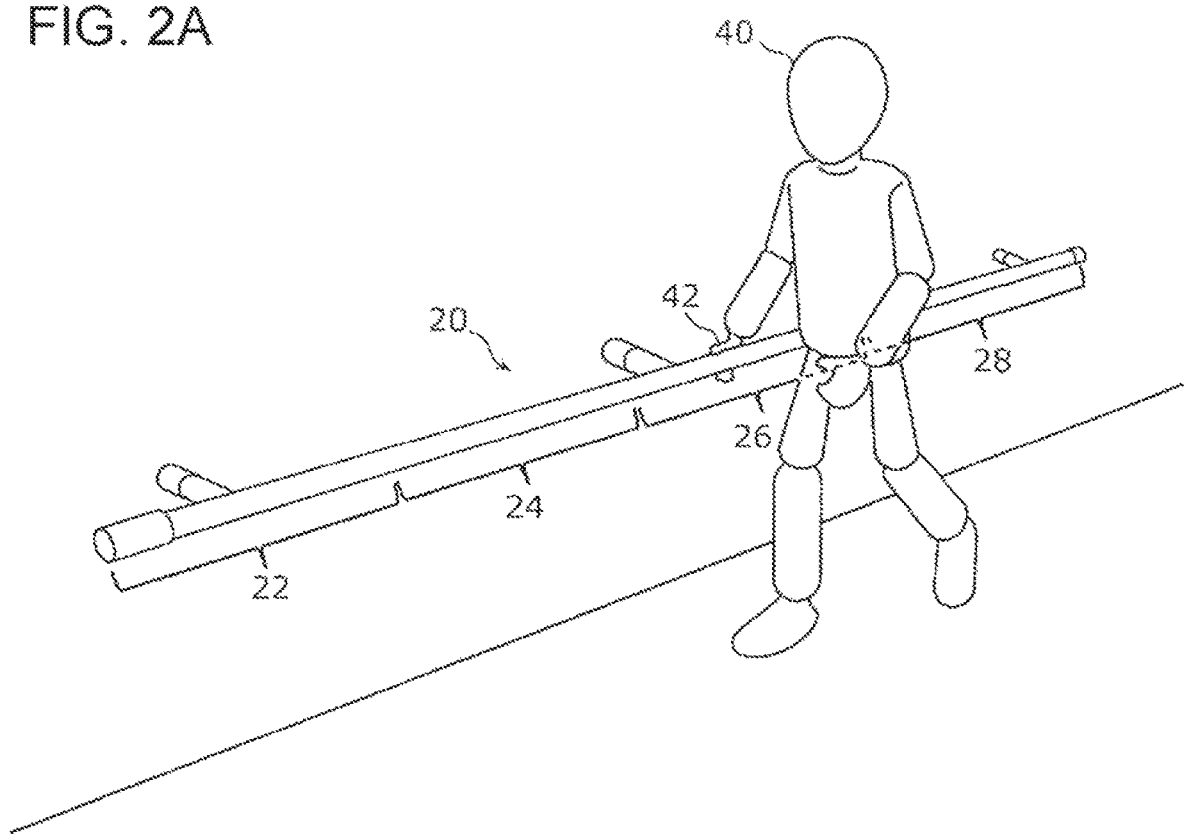
FIG. 2A is a view illustrating an example of an image taken by an imaging unit according to Embodiment 1.
Figure 2B:
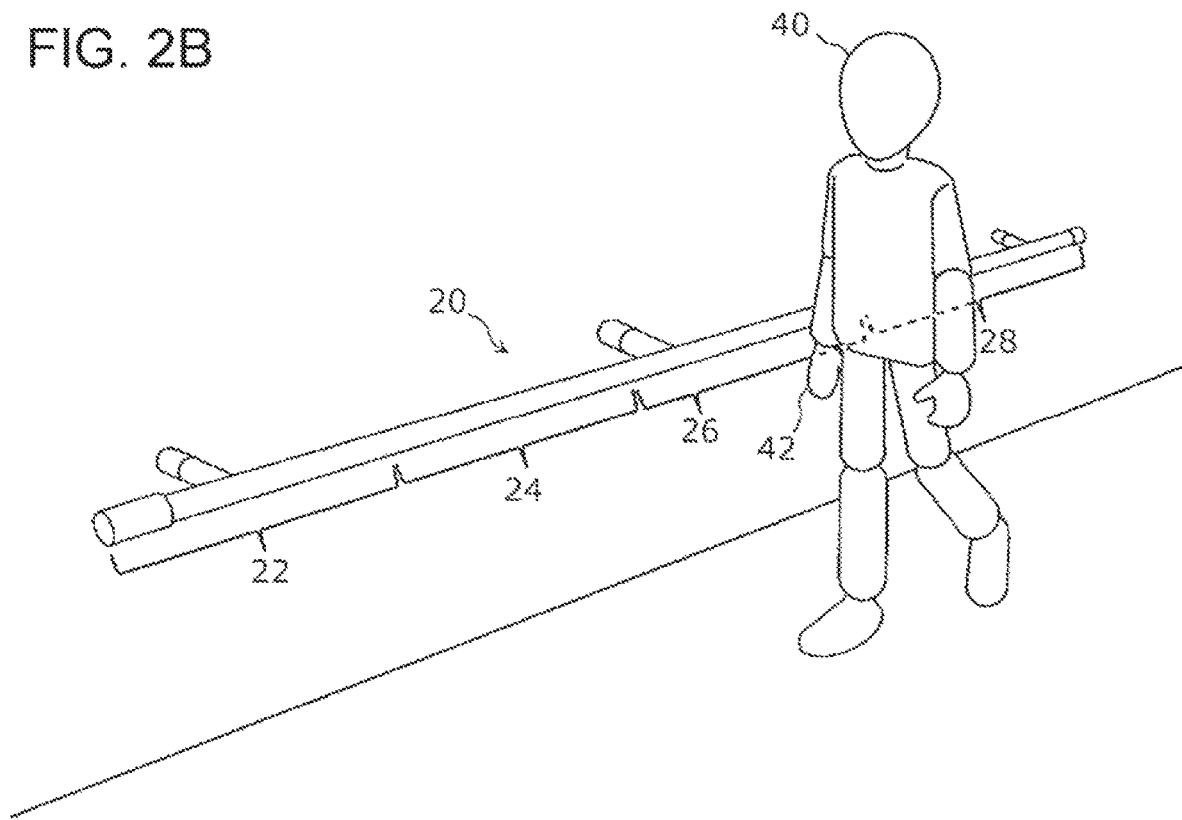
FIG. 2B is a view illustrating another example of an image taken by the imaging unit according to Embodiment 1.

At this point, examples of images taken by the imaging unit 300 will be described specifically with reference to FIGS. 2A and 2B. FIGS. 2A and 2B each illustrate an example of an image taken by the imaging unit 300 according to Embodiment 1. Specifically, FIG. 2A illustrates an image of a scene in which a hand 42 of a person 40 is contacting the handrail 20, while FIG. 2B illustrates an image of a scene in which the hand 42 of the person 40 is not contacting the handrail 20.

In the present embodiment, the handrail 20 is partitioned into multiple zones in advance. Herein, the zones include a first zone 22, a second zone 24, a third zone 26, and a fourth zone 28.

In consideration of cleaning work, the length of each zone may be a length that can be reached by the hand of the janitor without moving (for example, approximately 1 m) or less. Note that the length of each zone may exceed the length that can be reached by the hand of the janitor without the janitor moving.

The zones may be actually partitioned in a visually identifiable way, or the zones may be virtually partitioned. For example, the zones may be marked with different colors. As another example, the zones may be simply defined by digital data.

The imaging unit 300 takes an image of the equipment inside the nursing home and the person 40 inside the nursing home over time. The image may be successive still images or a moving image. The image includes one or more pieces of equipment. In FIG. 1, a digital video camera installed on the ceiling is illustrated as an example of the imaging unit 300. The imaging unit 300 may be a two-dimensional (2D) camera or a three-dimensional (3D) camera, for example. Any type of 3D technology may be used in the 3D camera. For example, the 3D camera may be a stereo camera, or a combination of a depth sensor and a 2D camera.

[Functional Configuration of Risk Evaluation System]

Figure 3:
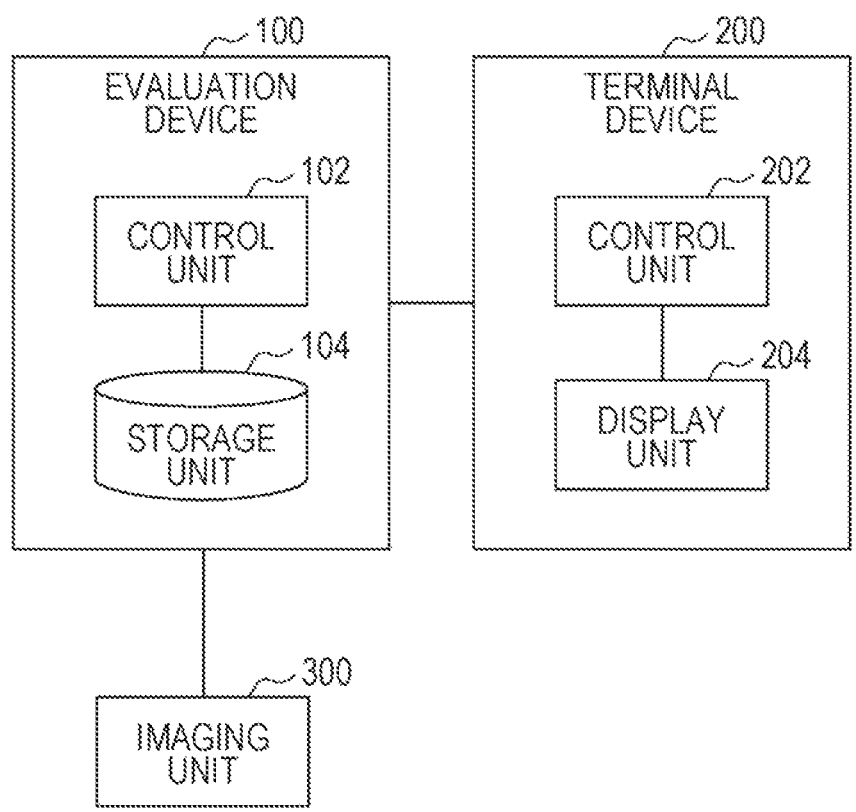
FIG. 3 is a block diagram illustrating a functional configuration of the risk evaluation system according to Embodiment 1.

Next, a functional configuration of the risk evaluation system will be described specifically with reference to FIG. 3. FIG. 3 is a block diagram illustrating a functional configuration of the risk evaluation system according to Embodiment 1. As illustrated in FIG. 3, the risk evaluation system is provided with an evaluation device 100, a terminal device 200, and the imaging unit 300.

[Functional Configuration of Evaluation Device]

The evaluation device 100 is a computer or an electronic circuit equipped with a processor and a memory for example, and is communicably connected to the terminal device 200 and the imaging unit 300. The evaluation device 100 is provided with a control unit 102 and a storage unit 104.

The control unit 102 is achieved by having the processor that executes a software program stored in the memory. The control unit 102 may be configured as a dedicated electronic circuit. The control unit 102 detects contact by a living body with each zone on the surface of each piece of equipment from images taken over time and output by the imaging unit 300. Additionally, the control unit 102 outputs evaluation information about the contact infection risk in each zone in accordance with the number of times contact is detected in each zone.

For example, the control unit 102 performs person detection in each image. Here, in the case where a person is detected from an image, the control unit 102 detects the position and posture of the person, for example. Technique of the related art such as machine learning may be used as the technique for detecting a person and the technique for detecting the position and posture of the person. More specifically, Kinect (registered trademark of Microsoft Corporation) can be used, for example.

In accordance with the detected position and posture of the person, the control unit 102 detects contact with each zone on an equipment surface by a part of the person. For example, the control unit 102 determines whether or not the distance between the detected position of the person and each zone is a threshold distance or less. At this point, in the case where the distance is the threshold distance or less, the control unit 102 determines whether or not the detected posture matches a predetermined posture. In the case where the detected posture matches a predetermined posture, the control unit 102 detects contact with the zone by a part of the person. For example, in the case where the distance between the detected person 40 and the third zone 26 of the handrail 20 is 40 cm or less, and the angle of the arm with respect to the torso is 10 degrees or more, the control unit 102 detects contact with the third zone 26 of the handrail 20 by the hand 42 of the person 40. As another example, in the case where the distance between the detected person 40 and the table 12 is 20 cm or less, and a posture of extending the hand 42 forward toward to the table 12 is detected, the control unit 102 detects contact with a surface zone of the table 12 by the hand 42 of the person 40. Also, in the case where the person 40 is sitting in the chair 14 in front of the table 12, and the angle of the arm with respect to the torso is 45 degrees or more, the control unit 102 detects contact with the surface zone of the table 12 by the hand 42 of the person 40.

In the case where contact is detected in this way, the control unit 102 increments a contact count for the corresponding zone by 1. The control unit 102 computes a risk value indicating how high the contact infection risk is in each zone in accordance with the contact count of each zone counted in this way. The risk value is a value that increases as the contact count increases. Furthermore, the control unit 102 outputs the computed risk value included in the evaluation information about the contact infection risk.

The storage unit 104 includes a hard disk drive and/or semiconductor memory, for example. The storage unit 104 stores zone information 106 that defines the zones on the surface of the equipment and contact information 108 that logs contact with each zone.

FIG. 4A illustrates an example of the zone information 106 in Embodiment 1. The zone information 106 includes information about equipment, zones, start points, and end points. For example, FIG. 4A demonstrates that a first zone of a handrail is in a distance range from 0 m to 1 m detected by the imaging unit 300.

FIG. 4B illustrates an example of the contact information 108 in Embodiment 1. The contact information 108 includes information about equipment, zones, contact counts, and contact dates and times. For example, FIG. 4B demonstrates that in a first zone of a handrail, contact has been detected 4 times.

[Functional Configuration of Terminal Device]

The terminal device 200 is a device with a display, such as a personal computer, a tablet computer, a smartphone, or a head-mounted display, for example. The terminal device 200 outputs evaluation information received from the evaluation device 100. In the present embodiment, the terminal device 200 is provided with a control unit 202 and a display unit 204.

The control unit 202 is achieved by having a processor that executes a software program stored in memory. The control unit 202 may be configured as a dedicated electronic circuit. The control unit 202 causes the display unit 204 to display evaluation information about the contact infection risk overlaid onto an image of the nursing home interior. Specifically, the control unit 202 causes the display unit 204 to display evaluation information about each zone overlaid onto the corresponding zone in the image.

The display unit 204 may be realized by a liquid crystal display or an organic EL display, for example. The display unit 204 is controlled by the control unit 202, and displays evaluation information about the contact infection risk.

[Operation of Risk Evaluation System]

Next, the operation of the evaluation device 100 included in the risk evaluation system configured as above will be described with reference to the drawings. The processes in the evaluation device 100 mainly include a contact information process related to information processing when detecting contact, and an evaluation information process related to information processing when outputting evaluation information.

[Contact Information Process]

Figure 5:
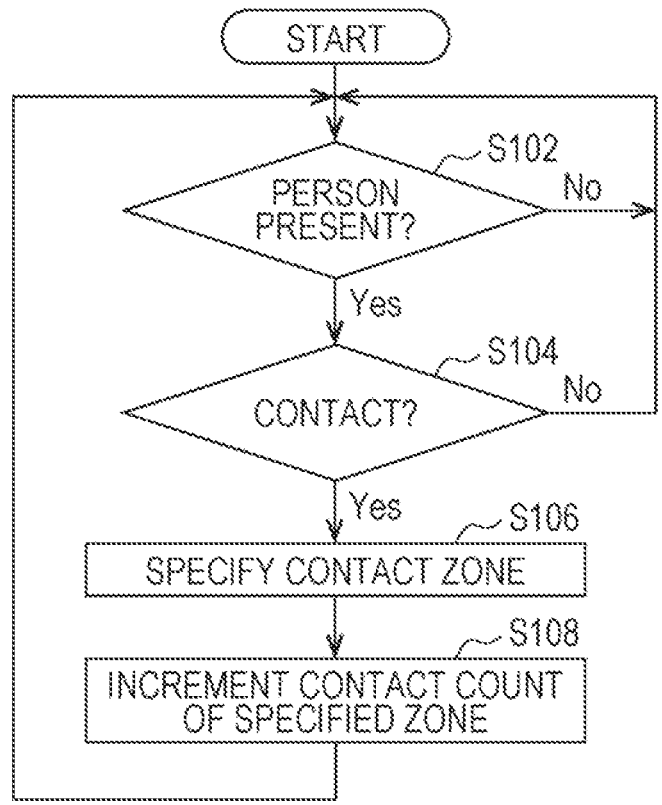
FIG. 5 is a flowchart illustrating a contact information process by an evaluation device according to Embodiment 1.

Accordingly, first, the contact information process will be described with reference to FIG. 5. FIG. 5 is a flowchart illustrating the contact information process by the evaluation device 100 according to Embodiment 1. The contact information process is executed continually over time.

First, the control unit 102 determines whether or not a person is present in the image taken by the imaging unit 300 (S102). Specifically, the control unit 102 performs person detection for example on the image taken by the imaging unit 300.

Here, in the case of determining that a person is not present in the image (S102, No), the control unit 102 repeats step S102. On the other hand, in the case of determining that a person is present in the image (S102, Yes), the control unit 102 determines whether or not there is contact with the surface of equipment by the person (S104). Specifically, the control unit 102 detects the position and posture of the person from the image for example, and determines whether or not there is contact with the surface of equipment by the person in accordance with the detected position and posture.

Here, in the case of determining that there is no contact with the equipment surface (S104, No), the flow returns to step S102. On the other hand, in the case of determining that there is contact with the equipment surface (S104, Yes), the control unit 102 specifies the zone that the person is contacting from among the zones (S106). Specifically, the control unit 102 references the zone information 106 illustrated in FIG. 4A for example, and specifies the zone corresponding to the detected position of the person as the zone that the person's hand is contacting.

Finally, the control unit 102 increments the contact count of the specified zone by 1 (S108). Specifically, in the contact information 108 illustrated in FIG. 4B for example, the control unit 102 logs the date and time of the contact and increases the value of the contact count by 1 for the specified zone.

According to such a contact information process, the contact count for each zone is counted.

[Evaluation Information Process]

Figure 6:
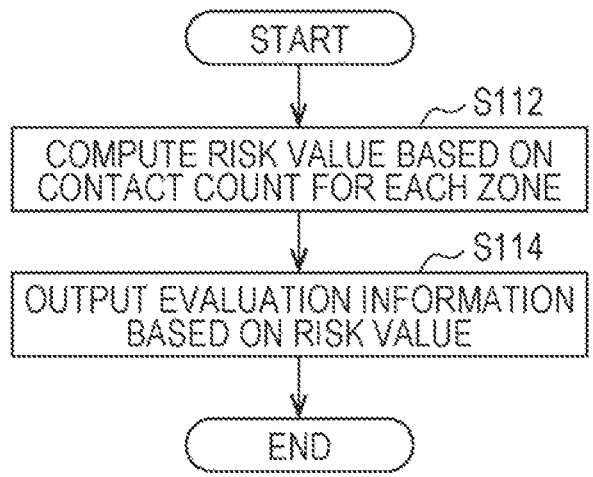
FIG. 6 is a flowchart illustrating an evaluation information process by the evaluation device according to Embodiment 1.

Next, the evaluation information process will be described with reference to FIG. 6. FIG. 6 is a flowchart illustrating the evaluation information process by the evaluation device 100 according to Embodiment 1. The evaluation information process is performed when appropriate according to demand. For example, the evaluation information process is performed in response to a request from a user.

As another example, the evaluation information process may be performed periodically on a predetermined cycle.

First, for each zone, the control unit 102 computes a risk value indicating how high the contact infection risk is in each zone in accordance with the contact count for each zone (S112). The control unit 102 may increase the risk value with respect to a higher contact count for each zone. For example, the control unit 102 computes the risk value by weighting the contact count using a weight value. A weight value refers to a value that is multiplied by the contact count and/or a value that is added to the contact count.

The weight value is a value set for each piece of equipment and/or each zone according to how high the contact infection risk is, for example. The weight value may be set manually by an administrator, or automatically in accordance with a past contact history.

For example, a larger value is used as the weight value with respect to zones and/or equipment having a higher probability of being contacted by many people. As another example, a larger value may be used as the weight value with respect to zones and/or equipment contacted more times in the past. As another example, a larger value may be used as the weight value in cases where an infectious disease has broken out in a neighboring area and/or cases where one or more persons claiming to feel unwell are present inside the facility. As another example, to suitably evaluate the contact infection risk due to a pathogen such as norovirus, a larger value may be used as the weight value with respect to zones and equipment closer to toilets and dining halls.

Next, the control unit 102 outputs evaluation information about the contact infection risk in accordance with the computed risk values (S114). For example, the control unit 102 transmits information associating computed risk values with zones to the terminal device 200 as the evaluation information. In this case, the control unit 202 of the terminal device 200 may cause the display unit 204 to display the evaluation information overlaid onto an image of the nursing home interior.

Figure 7:
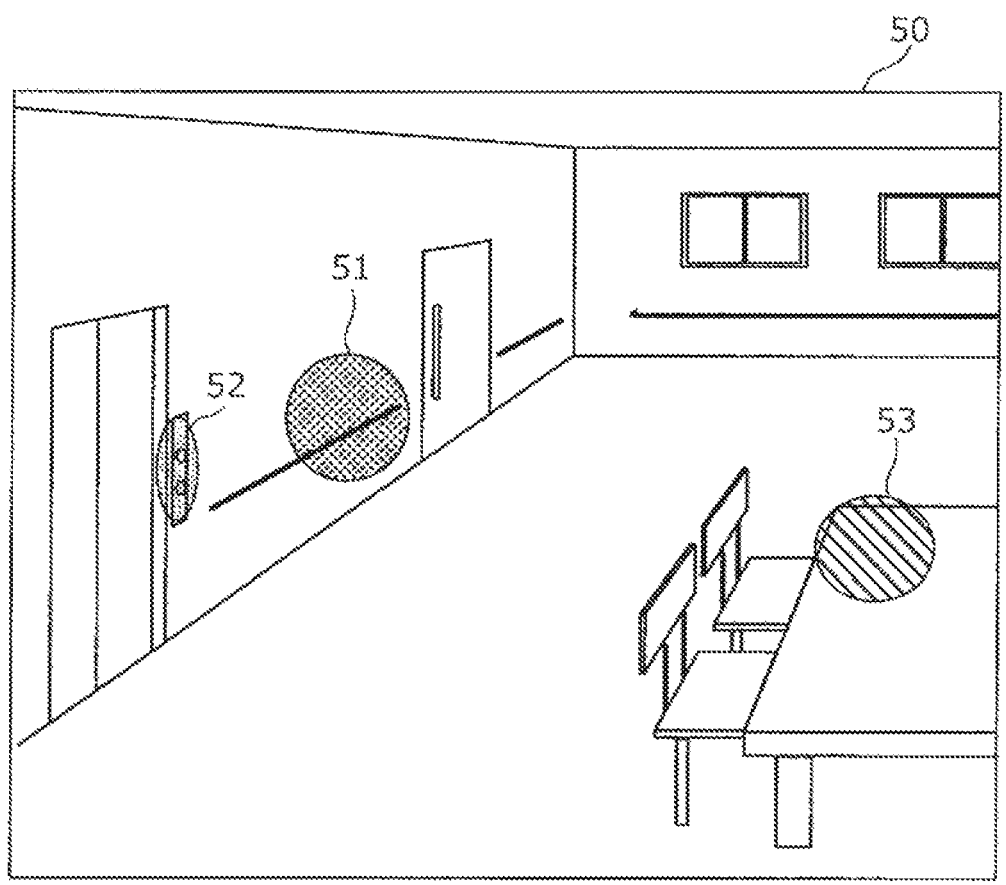
FIG. 7 is a view illustrating an exemplary display of evaluation information in Embodiment 1.

FIG. 7 illustrates an exemplary display of evaluation information in Embodiment 1. In FIG. 7, the control unit 202 is causing the display unit 204 to display, as the evaluation information, marks 51 to 53 marked with semi-transparent colors corresponding to the risk values overlaid onto an image 50 of the nursing home interior.

The image 50 of the nursing home interior may be an image stored in advance in the terminal device 200. Also, in the case where the terminal device 200 includes a camera, the image 50 of the nursing home interior may be an image taken by the camera. In this case, the control unit 202 may use augmented reality (AR) technology to display the evaluation information added to an image taken by the camera. For example, the control unit 202 can add the evaluation information to the image by detecting the equipment. The method of detecting the equipment is not particularly limited, but dedicated markers to detection that are physically attached to the equipment may be used.

Advantageous Effects and the Like

As above, according the risk evaluation system according to the present embodiment, it is possible to detect contact with each zone by a living body from multiple images, and output evaluation information about the contact infection risk in each zone in accordance with the detected contact count. Consequently, it is possible to perform cleaning work in each zone according to the evaluation information about the contact infection risk, and contribute to more efficient cleaning work for reducing contact infection.

Also, according to the risk evaluation system according to the present embodiment, a risk value computed in accordance with the contact count can be included in the evaluation information. Consequently, it is possible to perform cleaning work in each zone according to the magnitude of the risk value, and contribute to more efficient cleaning work for reducing contact infection.

Also, according to the risk evaluation system according to the present embodiment, the evaluation information can be displayed overlaid onto an image of the equipment. Consequently, the janitor can intuitively grasp locations that need to be cleaned, and even more efficient cleaning work can be achieved.

Note that in the present embodiment, the process by which the contact count is reset to 0 is not particularly described, but it is not necessary for the process to be particularly limited. For example, the risk evaluation system may reset the contact count of all zones to 0 in the case where reset input is received manually from the janitor. Note that the reset input may be performed for each piece of equipment and/or each zone. Also, the risk evaluation system may reset the contact count of all zones to 0 periodically and automatically.

Embodiment 2

Next, Embodiment 2 will be described. The main differences between the present embodiment and Embodiment 1 are that it is determined whether or not the contact with equipment is contact associated with cleaning work, and the contact count is reset to 0 depending on the detection result, and also that a cleaning instruction is issued to a terminal device. Hereinafter, the risk evaluation system according to the present embodiment will be described specifically with reference to the drawings, and mainly regarding the points that differ from Embodiment 1.

[Functional Configuration of Risk Evaluation System]

Figure 8:
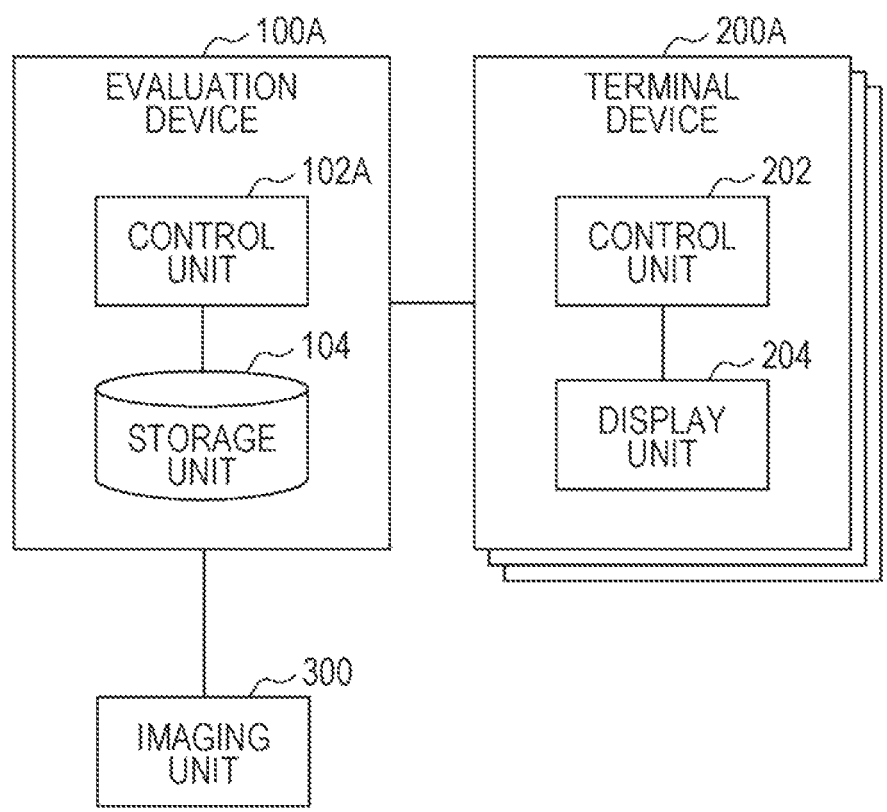
FIG. 8 is a block diagram illustrating a functional configuration of a risk evaluation system according to Embodiment 2.

First, the risk evaluation system according to the present embodiment will be described specifically with reference to FIG. 8. FIG. 8 is a block diagram illustrating a functional configuration of the risk evaluation system according to Embodiment 2. The risk evaluation system according to the present embodiment is provided with an evaluation device 100A, terminal devices 200A, and the imaging unit 300.

[Functional Configuration of Evaluation Device]

The evaluation device 100A is a computer or an electronic circuit equipped with a processor and a memory for example, and is communicably connected to the terminal devices 200A and the imaging unit 300. The evaluation device 100A is provided with a control unit 102A and the storage unit 104.

The control unit 102A is achieved by having the processor that executes a software program stored in the memory. The control unit 102A may be configured as a dedicated electronic circuit.

The control unit 102A according to the present embodiment determines whether or not contact with a zone on the surface of equipment detected by the imaging unit 300 is contact associated with cleaning work. Here, in the case of determining that the contact with the zone is contact associated with cleaning work, the control unit 102A resets the contact count of the zone to 0.

Note that cleaning work often involves repeating motions, such as the motion of wiping a cloth or the like back and forth over the surface of equipment.

Consequently, the control unit 102A can detect cleaning work by detecting repeating motions. In other words, by detecting repeating motions associated with cleaning in images taken over time by the imaging unit 300, the control unit 102A is capable of determining whether or not the contact with a zone is contact associated with cleaning work.

Furthermore, in the case of determining that the contact with a zone is not contact associated with cleaning work, the control unit 102A according to the present embodiment computes a risk value indicating how high the contact infection risk is in the zone in accordance with the contact count of the zone. In addition, the control unit 102A determines whether or not the computed risk value is greater than a predetermined threshold value. Here, in the case where the computed risk value is greater than the predetermined threshold value, the control unit 102A issues a cleaning instruction to clean the zone. For example, the control unit 102A acquires position information from each of the terminal devices 200A, and selects at least one terminal device from among the terminal devices 200A in accordance with the acquired position information. More specifically, the control unit 102A selects the terminal device closest to the zone from among the terminal devices 200A, for example. Subsequently, the control unit 102A issues the cleaning instruction to the at least one selected terminal device.

[Operation of Risk Evaluation System]

Next, the operation of the evaluation device 100A included in the risk evaluation system configured as above will be described with reference to the drawings. In the present embodiment, the contact information process that largely differs from Embodiment 1 will be described.

[Contact Information Process]

Figure 9:
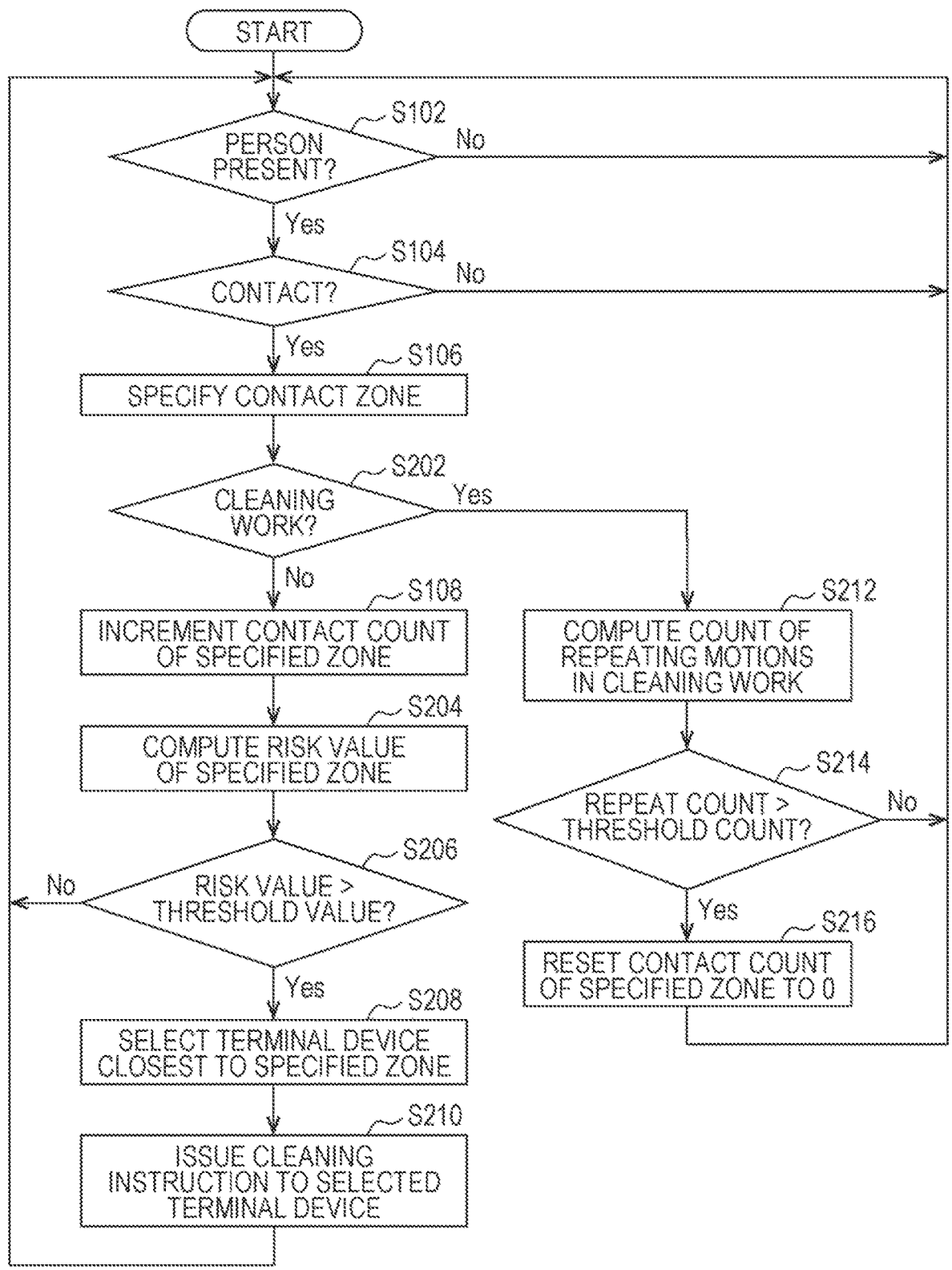
FIG. 9 is a flowchart illustrating a contact information process by an evaluation device according to Embodiment 2.

FIG. 9 is a flowchart illustrating the contact information process by the evaluation device 100A according to Embodiment 2. The contact information process is also executed continually over time.

First, like Embodiment 1, the control unit 102A determines whether or not a person is present in the image taken by the imaging unit 300 (S102). Here, in the case of determining that a person is not present in the image (S102, No), the control unit 102A repeats step S102. On the other hand, in the case of determining that a person is present in the image (S102, Yes), the control unit 102A determines whether or not there is contact with the surface of equipment by the person (S104). Furthermore, like Embodiment 1, the control unit 102A specifies the zone contacted by a hand from among the zones (S106).

The control unit 102A determines whether or not the contact with the specified zone is contact associated with cleaning work (S202). The determination is made by detecting repeating motions associated with cleaning work from the images taken by the imaging unit 300, for example.

Here, in the case of determining that the contact with the zone is not contact associated with cleaning work (S202, No), the control unit 102A increments the contact count of the specified zone by 1 (S108). Furthermore, the control unit 102A computes a risk value indicating how high the contact infection risk is in the specified zone in accordance with the incremented contact count (S204). The method of computing the risk value may be similar to step S112 in FIG. 6 of Embodiment 1. The control unit 102A determines whether or not the risk value is greater than a threshold value. Here, in the case where the risk value is the threshold value or less (S206, No), the flow returns to step S102.

In the case where the risk value is greater than the threshold value (S206, Yes), the control unit 102A selects at least one terminal device from among the terminal devices 200A (S208). For example, the control unit 102A acquires position information from each of the terminal devices 200A, and selects at least one terminal device from among the terminal devices 200A in accordance with the acquired position information about each of the terminal devices 200A. For example, the control unit 102A can select the terminal device closest to the specified zone from among the terminal devices 200A. As another example, the control unit 102A may select all terminal devices positioned within the range of a predetermined distance from the specified zone from among the terminal devices 200A.

For the acquisition of position information about the terminal devices 200A, if the terminal devices 200A are mobile terminals, a wireless communication technology (such as Wi-Fi (registered trademark) or Bluetooth (registered trademark), for example) or a technology such as the global positioning system (GPS) can be used.

After that, the control unit 102A issues a cleaning instruction to perform cleaning work in the specified zone to the selected terminal device (S210), and the flow returns to step S102. In each terminal device notified of the cleaning instruction, the user of the terminal device is informed of the cleaning instruction by sound, vibration, light, or some other informing means typically provided in a mobile terminal. For example, like the evaluation information in FIG. 7, the cleaning instruction may be displayed on the display unit 204, overlaid onto the image 50 of the nursing home interior. Also, the terminal device may use AR technology to display cleaning information (for example, zone information and cleaning method information) added to an image taken by the camera.

On the other hand, in the case of determining that the contact with the zone is contact associated with cleaning work (S202, Yes), the control unit 102A derives a count of the number of repeating motions in the cleaning work (S212). Next, the control unit 102A determines whether or not the derived repeat count is greater than a threshold count (S214). Also, for example, a count that is decided adaptively in accordance with the risk value or the contact count of the specified zone may be used as the threshold count. In this case, the threshold count may be set to 10 times when the risk value is high, and the threshold count may be set to 5 times when the risk value is low, for example.

Here, in the case where the repeat count is the threshold count or less (S214, No), the flow returns to step S102. On the other hand, in the case where the repeat count is greater than the threshold count (S214, Yes), the control unit 102A resets the contact count of the specified zone to 0 (S216), and the flow returns to step S102.

Advantageous Effects and the Like

As above, according to the risk evaluation system according to the present embodiment, it is possible to issue a cleaning instruction in the case where the risk value is greater than a threshold value. Consequently, an instruction to perform cleaning work in a zone with a high contact infection risk can be issued, and more efficient cleaning work for reducing contact infection can be achieved.

Also, according to the risk evaluation system according to the present embodiment, it is possible to issue a cleaning instruction to at least one terminal device selected from among the terminal devices 200A in accordance with position information about the terminal devices 200A. Consequently, the cleaning instruction can be issued to the terminal device of a user capable of performing the cleaning work efficiently according to the positional relationship with the zone, and more efficient cleaning work can be achieved.

Also, according to the risk evaluation system according to the present embodiment, in the case of determining that the contact with a zone by a hand is contact associated with cleaning work, the contact count of the zone can be reset to 0. Consequently, the reduction in the contact infection risk achieved by the cleaning work can be reflected in the evaluation information, making it possible to output more accurate evaluation information.

Also, according to the risk evaluation system according to the present embodiment, in the case where a repeat count of motions associated with the cleaning work exceeds a threshold count, the contact count of the zone can be reset to 0. Consequently, in the case where the motion is repeated enough to sufficiently reduce the contact infection risk, the contact count can be reset, and the contact infection risk can be reflected in the evaluation information more accurately.

Embodiment 3

Next, Embodiment 3 will be described. The main difference between the present embodiment and Embodiment 1 is that contact with the surfaces of the equipment by a body of a person is not only detected from an image taken over time by the imaging unit, but is also detected by a detection unit such as a distance sensor. Hereinafter, the risk evaluation system according to the present embodiment will be described specifically with reference to the drawings, and mainly regarding the points that differ from Embodiment 1.

[Exemplary Installation of Detection Unit]

Figure 10:
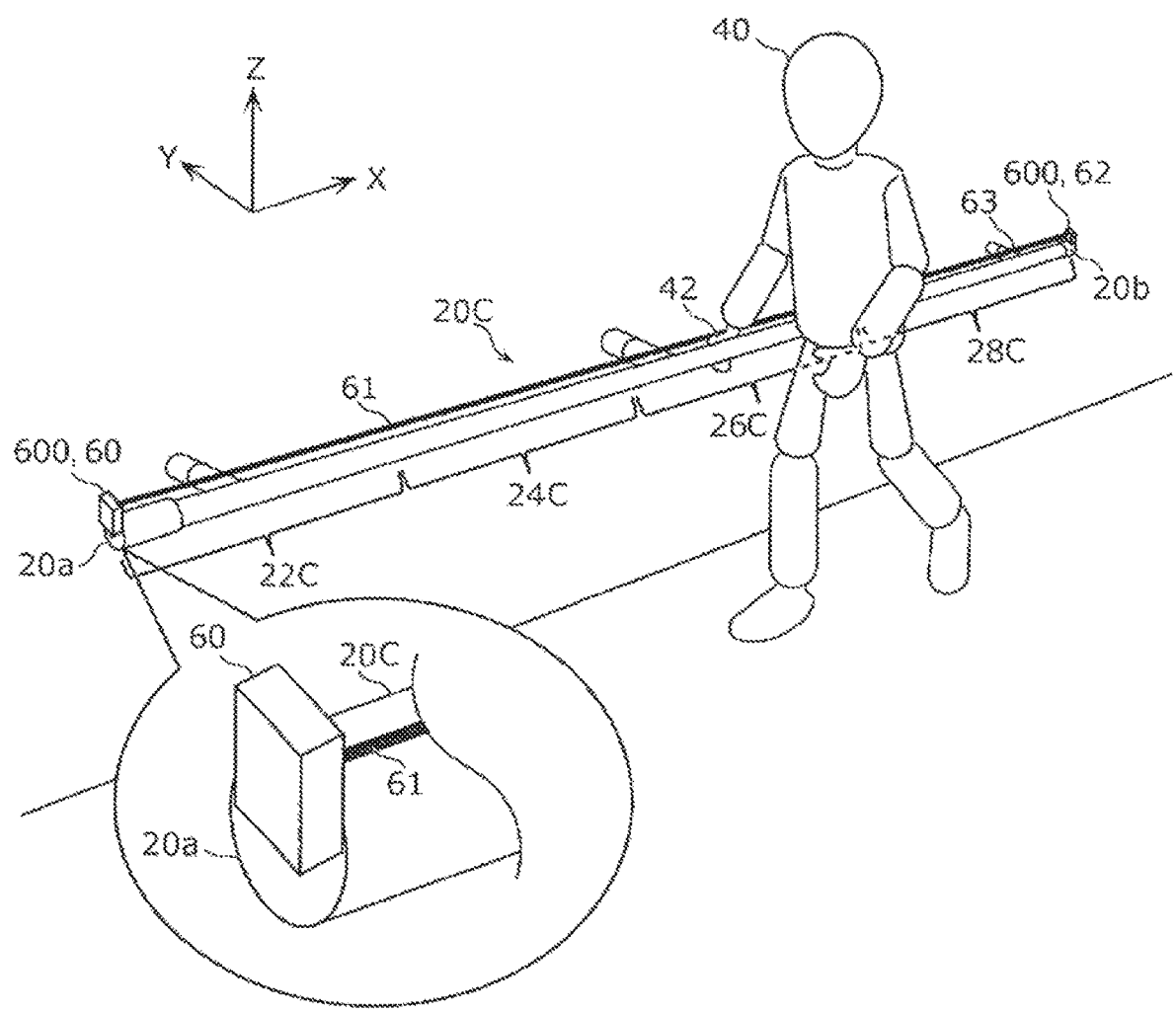
FIG. 10 is a view illustrating an exemplary installation of a detection unit according to Embodiment 3.

An exemplary installation of a detection unit will be described specifically with reference to FIG. 10. FIG. 10 is a diagram illustrating an exemplary installation of a detection unit 600 according to Embodiment 3. Specifically, FIG. 10 illustrates an exemplary installation of the detection unit 600 that detects contact with a handrail 20C by the hand 42 of the person 40. In FIG. 10, the X axis is the axis parallel to the longitudinal direction of the handrail 20C, the Y axis is the axis parallel to the transverse direction of the handrail 20C, and the Z axis is the axis perpendicular to the XY plane. Note that in FIG. 10, an example in which the detection unit 600 is installed in the handrail 20C is illustrated for the sake of convenience, but in Embodiment 3, because contact by a body can also be detected from the image taken by the imaging unit 300, it is desirable to install the detection unit 600 in a facility in a position less likely to be contained in the angle of view of the imaging unit 300 or in a facility not suited to being imaged by the imaging unit 300.

In the present embodiment, the handrail 20C is partitioned into zones in advance. Herein, the zones include a first zone 22C, a second zone 24C, a third zone 26C, and a fourth zone 28C.

In consideration of cleaning work, the length of each zone is desirably a length that can be reached by the hand of the janitor without moving (for example, approximately 1 m) or less. Note that the length of each zone may exceed the length that can be reached by the hand of the janitor without moving.

The zones may be actually partitioned in a visually identifiable way, or the zones may be virtually partitioned. For example, the zones may be marked with different colors. As another example, the zones may be simply defined by digital data alone.

The detection unit 600 is provided with a distance sensor that detects, in a non-contacting way, the distance to a target object (in FIG. 10, the hand 42 of the person 40) that is contacting the surface of the equipment. In the present embodiment, the distance sensor includes optical distance sensors 60 and 62.

The optical distance sensors 60 and 62 are installed at ends 20a and 20b in the longitudinal direction (the X-axis direction in FIG. 10) of the handrail 20C, and emit light beams 61 and 63 directed in opposite directions in the longitudinal direction of the handrail 20C along the surface of the handrail 20C. Specifically, the optical distance sensor 60 is installed on the negative X-axis end 20a of the handrail 20C, and emits the light beam 61 directed in the positive X-axis direction. On the other hand, the optical distance sensor 62 is installed on the positive X-axis end 20b of the handrail 20C, and emits the light beam 63 directed in the negative X-axis direction. With the light beams 61 and 63, the distance to the hand 42 of the person 40 contacting the surface of the handrail 20C is detected. For example, an infrared distance measuring module (manufactured by Sharp Corporation, serial number GP2Y0A21YK) can be used as the optical distance sensors 60 and 62.

Figure 11A:
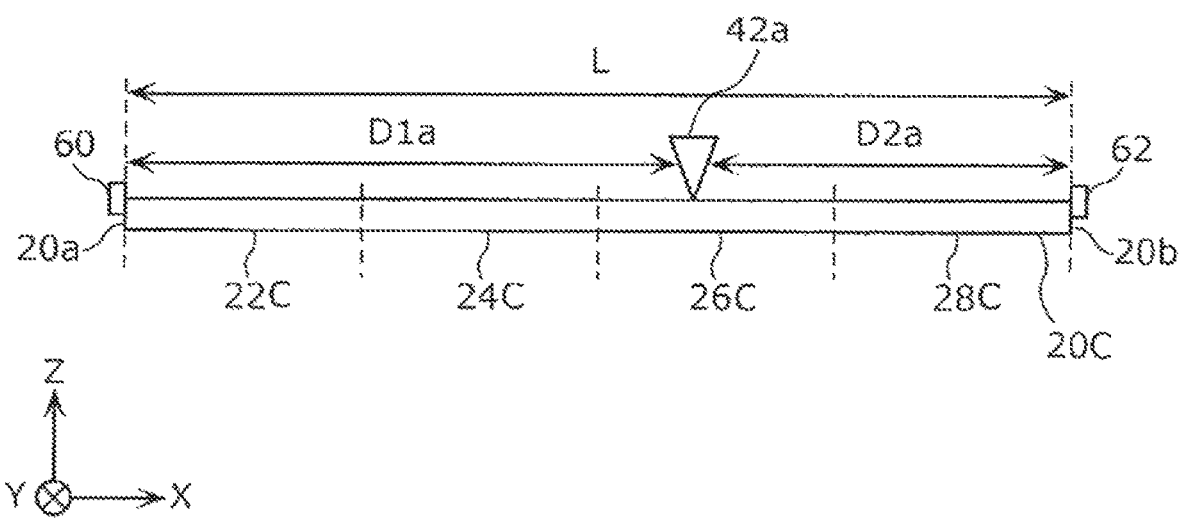
FIG. 11A is a diagram illustrating a state in which one hand is contacting the surface of a handrail in Embodiment 3.
Figure 11B:
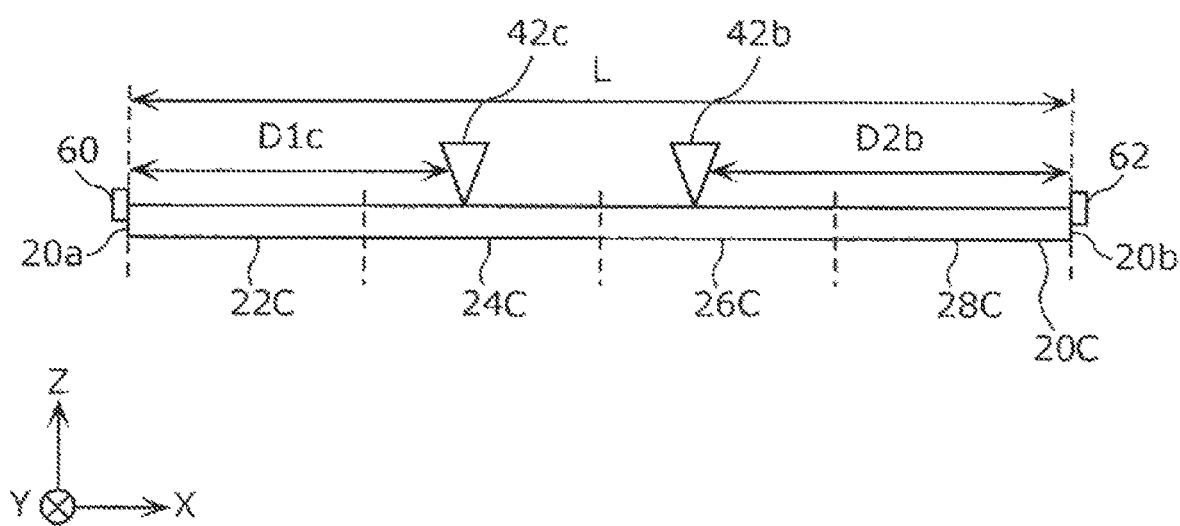
FIG. 11B is a diagram illustrating a state in which two hands are contacting the surface of a handrail in Embodiment 3.

The principle of contact detection using the optical distance sensors 60 and 62 will be described specifically with reference to FIGS. 11A and 11B. FIG. 11A illustrates a state in which one hand 42a is contacting the surface of the handrail 20C in Embodiment 3. FIG. 11B illustrates a state in which two hands 42b and 42c are contacting the surface of the handrail 20C in Embodiment 3. Note that in FIGS. 11A and 11B, L represents the total length of the handrail 20C, while D1a, D2a, D1c, and D2b represent the distances between each sensor and each hand.

As illustrated in FIG. 11A, in the case where the one hand 42a is contacting the third zone 26C, the optical distance sensors 60 and 62 detect the distances D1a and D2a. At this time, because the difference between the sum of the distances D1a and D2a and the total length L is sufficiently small, it is possible to detect that one hand is contacting the third zone 26C corresponding to the distances D1a and D2a.

On the other hand, as illustrated in FIG. 11B, in the case where the two hands 42b and 42c are contacting the third zone 26C and the second zone 24C, respectively, the optical distance sensors 60 and 62 detect the distances D c and D2b, respectively. At this time, because the difference between the sum of the distances D c and D2b and the total length L is large, it is possible to detect that two hands are contacting the second zone 24C corresponding to the distance D c and the third zone 26C corresponding to the distance D2b.

Figure 12A:
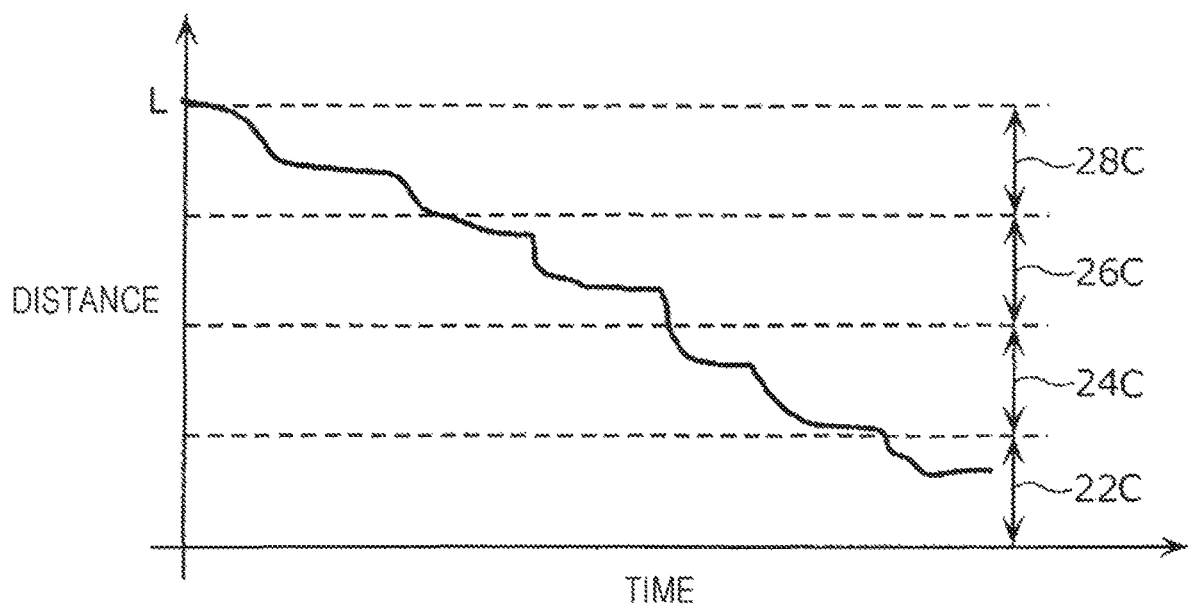
FIG. 12A is a graph illustrating an example of an output signal from an optical distance sensor in Embodiment 3.
Figure 12B:
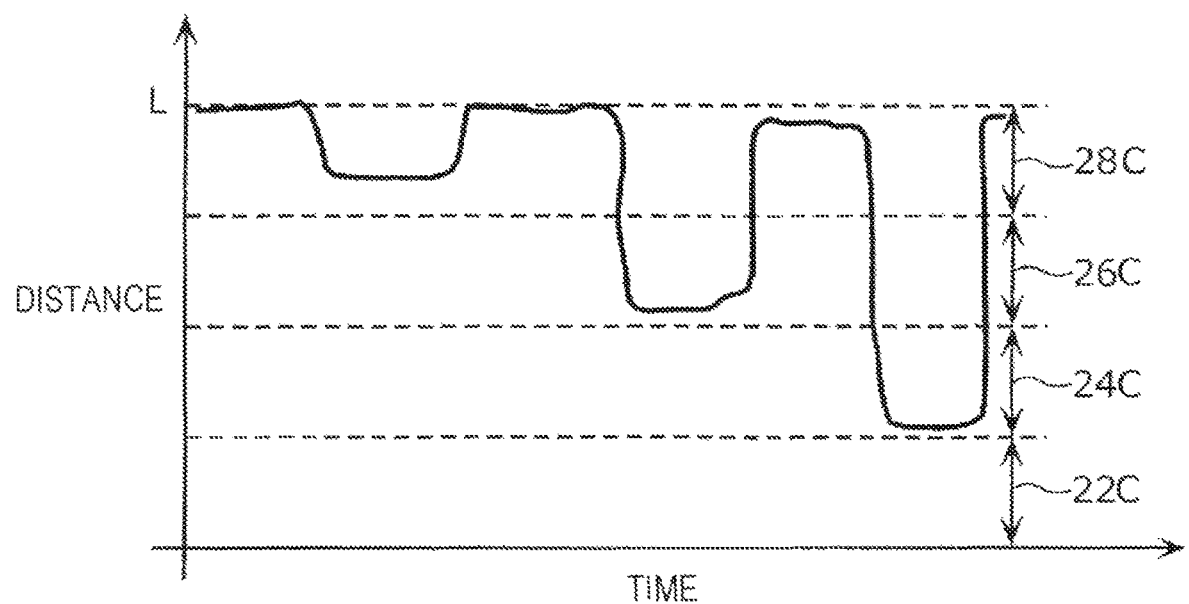
FIG. 12B is a graph illustrating an example of an output signal from the optical distance sensor in Embodiment 3.

Herein, examples of change over time in the distance expressed by the output signal from the optical distance sensor 60 will be described specifically with reference to FIGS. 12A and 12B. Each of FIGS. 12A and 12B is a graph illustrating an example of the output signal from the optical distance sensor 60 in Embodiment 3. In the graphs of FIGS. 12A and 12B, the horizontal axis represents time while the vertical axis represents distance. Also, the four distance ranges indicated by the dashed lines correspond to the first to fourth zones 22C to 28C in FIGS. 10 to 11B.

In FIG. 12A, the distance expressed by the output signal from the optical distance sensor 60 gradually decreases. This case indicates that the hand 42 is approaching the optical distance sensor 60 while contacting the surface of the handrail 20C. Also, in FIG. 12B, the distance expressed by the output signal from the optical distance sensor 60 intermittently decreases. This case indicates that the hand 42 is approaching the optical distance sensor 60 while alternately contacting and not contacting the surface of the handrail 20C.

[Functional Configuration of Risk Evaluation System]

Figure 13:
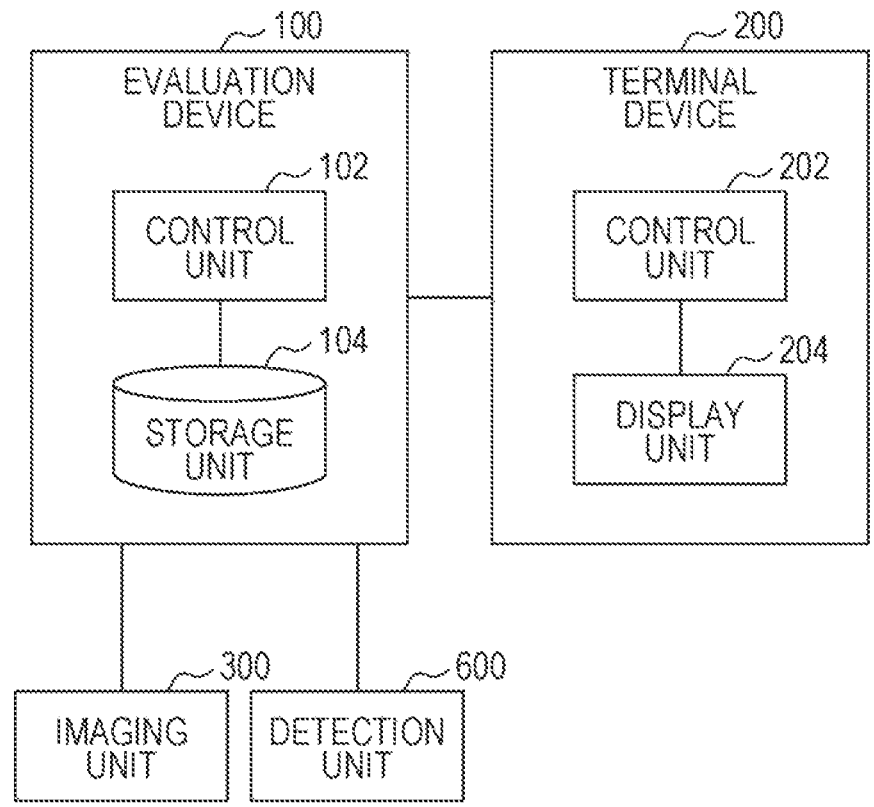
FIG. 13 is a block diagram illustrating a functional configuration of a risk evaluation system according to Embodiment 3.

Next, a functional configuration of the risk evaluation system will be described specifically with reference to FIG. 13. FIG. 13 is a block diagram illustrating a functional configuration of the risk evaluation system according to Embodiment 3. As illustrated in FIG. 13, the risk evaluation system is provided with the evaluation device 100, the terminal device 200, the imaging unit 300, and the detection unit 600.

[Functional Configuration of Evaluation Device]

The evaluation device 100 is communicably connected to the terminal device 200, the imaging unit 300, and the detection unit 600. The evaluation device 100 is provided with the control unit 102 and the storage unit 104.

The control unit 102 detects contact by a living body with each zone on the surface of each piece of equipment from images taken over time and output by the imaging unit 300. Additionally, the control unit 102 outputs evaluation information about the contact infection risk in each zone in accordance with the number of times contact is detected in each zone and the number of times contact with each zone is detected by the detection unit 600.

For example, the control unit 102 specifies a zone contacted by the hand 42 of the person 40 from among the first to fourth zones 22C to 28C in accordance with the distances detected by the optical distance sensors 60 and 62.

Additionally, the control unit 102 increments the contact count of the specified zone by 1. The control unit 102 computes a risk value indicating how high the contact infection risk is in each zone in accordance with the contact count of each zone counted in this way. The risk value is a value that increases as the contact count increases. For example, the control unit 102 may reference risk information associating contact counts with risk values, and compute the risk value corresponding to the number of times contact is detected by the detection unit 600. Furthermore, the control unit 102 outputs the computed risk value included in the evaluation information about the contact infection risk.

[Contact Information Process]

Figure 14:
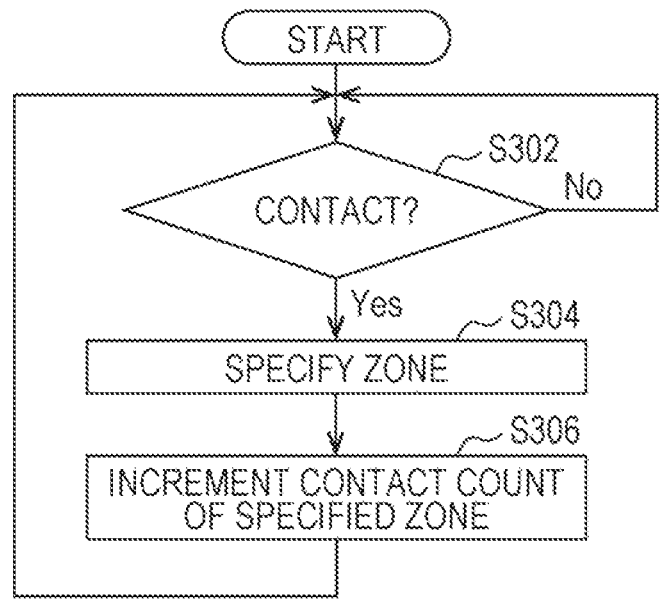
FIG. 14 is a flowchart illustrating a contact information process based on a detection result from a detection unit of an evaluation device according to Embodiment 3.

A contact information process will be described with reference to FIG. 14. FIG. 14 is a flowchart illustrating a contact information process based on a detection result from the detection unit 600 of the evaluation device 100 according to Embodiment 3. The contact information process is executed continually over time.

First, the control unit 102 acquires the output signal from the detection unit 600, and in accordance with the acquired output signal, determines whether or not there is contact with the surface of equipment (S302). Specifically, the control unit 102 determines whether or not there is contact with the surface of the equipment in accordance with a distance detected by the detection unit 600, for example.

Herein, in the case of determining that there is no contact with the equipment surface (S302, No), the control unit 102 repeats step S302. On the other hand, in the case of determining that there is contact with the equipment surface (S302, Yes), the control unit 102 specifies the zone that a hand is contacting from among the zones, in accordance with the distance detected by the detection unit 600 (S304). Specifically, the control unit 102 references the zone information 106 illustrated in FIG. 6A for example, and specifies the zone corresponding to the distance detected by the detection unit 600 as the zone that the hand is contacting.

Finally, the control unit 102 increments the contact count of the specified zone by 1 (S306). Specifically, in the contact information 108 illustrated in FIG. 6B for example, the control unit 102 logs the date and time of the contact and increases the value of the contact count by 1 for the specified zone.

According to such a contact information process, the contact count for each zone is counted. Note that the evaluation information process is substantially similar to Embodiment 1, and therefore omitted from description.

Advantageous Effects and the Like

As above, according the risk evaluation system according to the present embodiment, it is possible to detect contact with each zone by a living body from multiple images, output evaluation information about the contact infection risk in each zone in accordance with the detected contact count, and furthermore output evaluation information about the contact infection risk in accordance with a contact count detected by a detecting unit. Consequently, it is possible to output more accurate evaluation information.

Other Embodiments

The foregoing describes a risk evaluation system according to one or more aspects of the present disclosure in accordance with embodiments, but the present disclosure is not limited to the embodiments. Embodiments obtained by applying various modifications that may occur to persons skilled in the art as well as embodiments constructed by combining the structural elements in different embodiments may be included within the scope of the one or more aspects of the present disclosure, insofar as such embodiments do not depart from the gist of the present disclosure.

Although the foregoing embodiments describe the risk evaluation system by taking contact with a handrail inside a nursing home as an example, the equipment to which the risk evaluation system is applied is not limited to a handrail inside a nursing home. For example, as illustrated in FIG. 1, the risk evaluation system may be applied to the table 12, the chairs 14, the touch panel 16, and the door 18.

In the foregoing embodiments, the position and posture of a person is detected to detect contact with an equipment surface by a hand, but the contact detection is not limited thereto. For example, in the case where a 3D camera is used, the control unit can detect contact with the equipment surface by the hand from position information about the hand in an image. As another example, in the case of detecting whether or not a hand of a person has contacted the handle of the door 18, it may be detected whether or not the person has passed through the doorway of the door 18. In this case, the phenomenon of the person passing through the doorway can be interpreted as a phenomenon in which the person's hand has contacted the handle of the door 18. In other words, when it is detected that the person has passed through the doorway, the contact count is incremented.

Although the foregoing embodiments describe the risk of contact infection from person to person via the surface of equipment, the source of infection is not limited to a person. For example, the risk of contact infection from an animal (such as a dog or a cat for example) to a person may be evaluated. In this case, it is sufficient for the control unit to also detect contact by the animal with each zone on the surface of the equipment. In other words, it is sufficient for the control unit to detect contact by a living body.

In the foregoing embodiments, the surface of a single piece of equipment is partitioned into zones, but the surface of a single piece of equipment may be a single zone. Furthermore, the number of zones may be different depending on the equipment.

In the foregoing embodiments, the contact count is included in the contact information, but is not limited thereto. The contact count may be computed as necessary. For example, the contact count may be computed every time contact is detected or every time an instruction to output the evaluation information is received, in accordance with the contact date and time.

In the foregoing embodiments, the evaluation device is described as a single device, but is not limited thereto. For example, the evaluation device may be realized by distributed computing or cloud computing.

In the foregoing embodiments, the terminal device is included in the risk evaluation system, but the terminal device does not have to be included in the risk evaluation system. In this case, the evaluation device may achieve the functions of the terminal device, for example.

In the foregoing embodiments, the risk value is used, but it is not strictly necessary to use the risk value. For example, the contact count may be used instead of the risk value. In this case, the computation of the risk value may be omitted.

In Embodiment 2 above, a cleaning instruction is issued to the terminal device to instruct the janitor to clean, but the configuration is not limited thereto. For example, the cleaning instruction may be issued to a cleaning robot. In this case, it is sufficient for the cleaning robot to clean the zone corresponding to the cleaning instruction automatically.

In Embodiment 2 above, the cleaning instruction is issued to one or more terminal devices selected from among the terminal devices 200A, but the configuration is not limited thereto. For example, the cleaning instruction may be issued to all of the terminal devices 200A. As another example, in the case of selecting the terminal device positioned within the range of a predetermined distance from the specified zone, if no terminal device exists within the range, the selection of the terminal device and the issuing of the cleaning instruction may be postponed. In this case, when a terminal device enters the range, it is sufficient to issue the cleaning instruction to the terminal device. As another example, duty or shift information about who is in charge of cleaning on each day or time or day may be preregistered in the storage unit 104 of the evaluation device 100, and the cleaning instruction may be issued to the terminal device 200A carried by the janitor in charge according to the day or time of day.

In Embodiment 2 above, the cleaning work is determined in accordance with the result of detecting repeating motions, but the determination is not limited thereto. For example, the cleaning work may be determined by performing face recognition on the janitor in the image taken by the imaging unit 300. Alternatively, the cleaning work may be determined by detecting cleaning gloves in the image.

Note that the display of the evaluation information in FIG. 7 is an example and non-limiting. The evaluation information may be displayed in words, for example. Specifically, the evaluation information may be displayed as text information including a zone name and the risk value. In this case, the color or the display order of the words may be changed according to the risk value. For example, the evaluation information may be displayed as a list in order of descending risk value. The zone names may be a name that covers multiple zones, enabling the user to specify locations easily. One example of a name that covers multiple zones is "the zones of the handrail from the dining hall door to the toilet door on the first floor".

In Embodiment 3 above, optical distance sensors are used as the distance sensor, but the distance sensor is not limited thereto. The distance sensor may be an ultrasonic sensor, for example. Also, the number and arrangement of distance sensors is not limited to the example illustrated in FIG. 10.

For example, a single distance sensor capable of detecting distance in two directions may be provided in a middle part of the handrail 20C. Additionally, the distance sensor may be provided in each zone.

The present disclosure can be used as a risk evaluation system for improving the efficiency of cleaning work for equipment and the like inside a nursing home.

What is claimed is:

1. A risk evaluation system comprising:
a camera that takes images at different times of a continuous handrail having zones that do not overlap each other, and outputs the images that are taken;
a distance sensor that detects contact by a living body with each of the zones of the continuous handrail that do not overlap each other; and
a processor that
(i) detects a contact count of a number of times the living body contacts each of the zones in accordance with the images,
(ii) decides evaluation information about a contact infection risk in each of the zones of the continuous handrail in accordance with (a) the contact count of the number of times the living body contacts each of the zones of the continuous handrail in accordance with the images and (b) a number of times the contact by the living body with each of the zones of the continuous handrail is detected by the distance sensor, and
(iii) outputs the evaluation information,
wherein the distance sensor includes (i) a first optical distance sensor installed on a first end of the continuous handrail in a longitudinal direction of the continuous handrail and (ii) a second optical distance sensor installed on a second end of the continuous handrail in the longitudinal direction of the continuous handrail,
the first optical distance sensor emits a first light beam in a direction from the first end of the continuous handrail to the second end of the continuous handrail, and the second optical distance sensor emits a second light beam in a direction from the second end of the continuous handrail to the first end of the continuous handrail, and
the contact by the living body and one of the zones that the living body is contacting is detected in accordance with a distance to the living body contacting the continuous handrail detected according to the first light beam and the second light beam.

2. The risk evaluation system according to claim 1, wherein
the processor additionally computes, for each zone, a risk value indicating how high the contact infection risk is in accordance with a number of times contact occurs, and
the evaluation information includes the risk value that is computed.

3. The risk evaluation system according to claim 2, wherein
for each zone, the processor additionally
(i) determines whether or not the risk value that is computed is greater than a predetermined threshold value, and
(ii) issues a cleaning instruction to clean the zone in a case where the risk value that is computed is greater than the predetermined threshold value.

4. The risk evaluation system according to claim 3, wherein
the processor
acquires position information about terminal devices,
selects at least one terminal device among the terminal devices in accordance with the position information about the terminal devices that is acquired, and
issues the cleaning instruction to the at least one terminal device that is selected.

5. The risk evaluation system according to claim 1, wherein
in a case that the detected contact with one of the zones by the living body is the contact associated with cleaning work, the processor resets the contact count of the zone to 0.

6. The risk evaluation system according to claim 5, wherein
in a case that the detected contact with one of the zones by the living body is the contact associated with the cleaning work, the processor additionally
(i) derives a repeat count of motions associated with the cleaning work, and
(ii) resets the contact count of the one of the zones to 0 in a case where the repeat count that is derived is greater than a threshold count.

7. The risk evaluation system according to claim 1, further comprising:
a terminal device, wherein
the processor outputs the evaluation information to the terminal device.

8. The risk evaluation system according to claim 7, wherein
the terminal device displays the evaluation information overlaid onto an image of the continuous handrail.

9. A risk evaluation method comprising:
taking, using a camera, images at different times of a continuous handrail having zones that do not overlap each other, and outputting the images that are taken;
detecting, using a distance sensor, contact by a living body with each of the zones of the continuous handrail that do not overlap each other;
detecting a contact count of a number of times the living body contacts each of the zones of the continuous handrail in accordance with the images;
deciding evaluation information about a contact infection risk in each of the zones in accordance with (a) the contact count of the number of times the living body contacts each of the zones of the continuous handrail in accordance with the images and (b) a number of times the contact by the living body with each of the zones of the continuous handrail is detected; and
outputting the evaluation information,
wherein the distance sensor includes (i) a first optical distance sensor installed on a first end of the continuous handrail in a longitudinal direction of the continuous handrail and (ii) a second optical distance sensor installed on a second end of the continuous handrail in the longitudinal direction of the continuous handrail,
the first optical distance sensor emits a first light beam in a direction from the first end of the continuous handrail to the second end of the continuous handrail, and the second optical distance sensor emits a second light beam in a direction from the second end of the continuous handrail to the first end of the continuous handrail, and
the contact by the living body and one of the zones that the living body is contacting is detected in accordance with a distance to the living body contacting the continuous handrail detected according to the first light beam and the second light beam.

10. A non-transitory computer-readable recording medium storing a program causing a computer to execute a risk evaluation method, the risk evaluation method comprising:
taking, using a camera, images at different times of a continuous handrail having zones that do not overlap each other, and outputting the images that are taken;
detecting, using a distance sensor, contact by a living body with each of the zones of the continuous handrail that do not overlap each other;
detecting a contact count of a number of times the living body contacts each of the zones of the continuous handrail in accordance with the images;
deciding evaluation information about a contact infection risk in each of the zones in accordance with (a) the contact count of the number of times the living body contacts each of the zones of the continuous handrail in accordance with the images and (b) a number of times the contact by the living body with each of the zones of the continuous handrail is detected; and
outputting the evaluation information,
wherein the distance sensor includes (i) a first optical distance sensor installed on a first end of the continuous handrail in a longitudinal direction of the continuous handrail and (ii) a second optical distance sensor installed on a second end of the continuous handrail in the longitudinal direction of the continuous handrail,
the first optical distance sensor emits a first light beam in a direction from the first end of the continuous handrail to the second end of the continuous handrail, and the second optical distance sensor emits a second light beam in a direction from the second end of the continuous handrail to the first end of the continuous handrail, and
the contact by the living body and one of the zones that the living body is contacting is detected in accordance with a distance to the living body contacting the continuous handrail detected according to the first light beam and the second light beam.

* * * * *